US012157666B2

United States Patent
Dayeh et al.

(10) Patent No.: US 12,157,666 B2
(45) Date of Patent: Dec. 3, 2024

(54) SHARP, VERTICALLY ALIGNED NANOWIRE ELECTRODE ARRAYS, HIGH-YIELD FABRICATION AND INTRACELLULAR RECORDING

(71) Applicant: The Regents of the University of California, Oakland, CA (US)

(72) Inventors: Shadi Dayeh, San Diego, CA (US); Ren Liu, Albuquerque, NM (US); Youngbin Tchoe, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 1066 days.

(21) Appl. No.: 17/052,055

(22) PCT Filed: May 8, 2019

(86) PCT No.: PCT/US2019/031316
§ 371 (c)(1),
(2) Date: Oct. 30, 2020

(87) PCT Pub. No.: WO2019/217553
PCT Pub. Date: Nov. 14, 2019

(65) Prior Publication Data
US 2021/0093246 A1    Apr. 1, 2021

Related U.S. Application Data

(60) Provisional application No. 62/669,639, filed on May 10, 2018.

(51) Int. Cl.
*B81C 1/00* (2006.01)
*A61B 5/00* (2006.01)
(Continued)

(52) U.S. Cl.
CPC ........ *B81C 1/00111* (2013.01); *A61B 5/0077* (2013.01); *A61B 5/25* (2021.01);
(Continued)

(58) Field of Classification Search
CPC ................ B81B 1/008; B81B 2203/04; B81C 2201/0178; B81C 1/00111
See application file for complete search history.

(56) References Cited

U.S. PATENT DOCUMENTS

| 7,905,013 B2 | 3/2011 | Zhang et al. |
| 8,372,752 B1 * | 2/2013 | Huang ................ H01L 29/0676 438/719 |

(Continued)

FOREIGN PATENT DOCUMENTS

| CN | 105679631 B * | 8/2018 | ......... G01N 23/2204 |
| WO | 2016112315 A3 | 7/2016 | |
| WO | 2017127551 A1 | 7/2017 | |

OTHER PUBLICATIONS

International Search Report and Written Opinion from the corresponding International Patent Application No. PCT/US2019/031316, dated Sep. 20, 2019.

(Continued)

*Primary Examiner* — Edward Chin
(74) *Attorney, Agent, or Firm* — Greer, Burns & Crain, Ltd.; Steven P. Fallon

(57) ABSTRACT

A nanowire electrode array has a plurality of vertical nanowires extending from a substrate, each of the nanowires including a core of unitary first dielectric material that also covers the substrate and is unitary with the substrate. Each core has a sharp sub-100 nm diameter tip and a wider base, electrode leads on sidewalls to the tip of the nanowire, and second dielectric covering the electrode leads. The tips in the array can penetrate individual cells in cell culture, such as a (Continued)

mini-brain culture. The substrate can include a window for simultaneous optical imaging and electrophysiological recording.

18 Claims, 17 Drawing Sheets

(51) Int. Cl.
*A61B 5/25* (2021.01)
*B81B 1/00* (2006.01)

(52) U.S. Cl.
CPC ...... *B81B 1/008* (2013.01); *A61B 2562/0285* (2013.01); *A61B 2562/046* (2013.01); *A61B 2562/125* (2013.01); *B81B 2203/04* (2013.01); *B81C 2201/0132* (2013.01); *B81C 2201/0178* (2013.01)

(56) References Cited

U.S. PATENT DOCUMENTS

| | | | |
|---|---|---|---|
| 11,363,979 B2 * | 6/2022 | Dayeh | A61B 5/24 |
| 2009/0127722 A1 * | 5/2009 | Noelscher | B81C 1/00111 |
| | | | 438/401 |
| 2010/0112373 A1 | 5/2010 | Coffey et al. | |
| 2012/0322164 A1 | 12/2012 | Lal et al. | |
| 2016/0284604 A1 * | 9/2016 | Chang | H01L 29/1037 |
| 2017/0231518 A1 | 8/2017 | Dayeh et al. | |
| 2018/0019122 A1 | 1/2018 | Guiton et al. | |
| 2018/0358226 A1 * | 12/2018 | Lee | H01L 21/02535 |
| 2019/0021619 A1 * | 1/2019 | Dayeh | B82Y 15/00 |
| 2020/0347393 A1 * | 11/2020 | Park | C12N 15/8207 |

OTHER PUBLICATIONS

Hodgkin et al., "Action Potentials Recorded from Inside a Nerve Fibre", Nature, Oct. 21, 1939, pp. 710-711, vol. 144, Nature Publishing Group.

Kim et al., "Nanoscale cues regulate the structure and function of macroscopic cardiac tissue constructs", PNAS, Jan. 12, 2010, pp. 565-570, vol. 107, No. 2, National Academy of Sciences.

Lin et al., "Iridium oxide nanotube electrodes for sensitive and prolonged intracellular measurement of action potentials", Nature Communications, Feb. 3, 2014, pp. 1-10, vol. 5, Macmillan Publishers Limited.

Liu et al., "High Density Individually Addressable Nanowire Arrays Record Intracellular Activity from Primary Rodent and Human Stem Cell Derived Neurons", Nano Letters, 2017, pp. 2757-2764, vol. 17, American Chemical Society.

Werner et al., "Surface Curvature Differentially Regulates Stem Cell Migration and Differentiation via Altered Attachment Morphology and Nuclear Deformation", Advanced Science News, 2017, pp. 1-11, vol. 4, Wiley-VCH Verlag GmbH & Co. KGaA, Weinheim.

Xie et al., "Intracellular recording of action potentials by nanopillar electroporation", Nature Nanotechnology, Mar. 2012, pp. 185-190, vol. 7, Macmillan Publishers Limited.

* cited by examiner

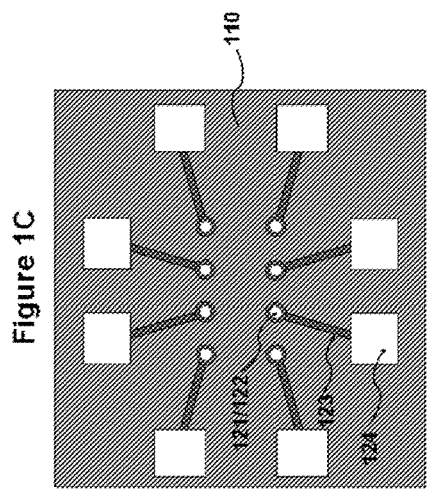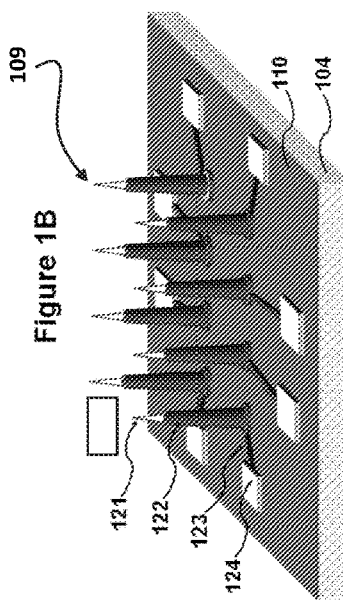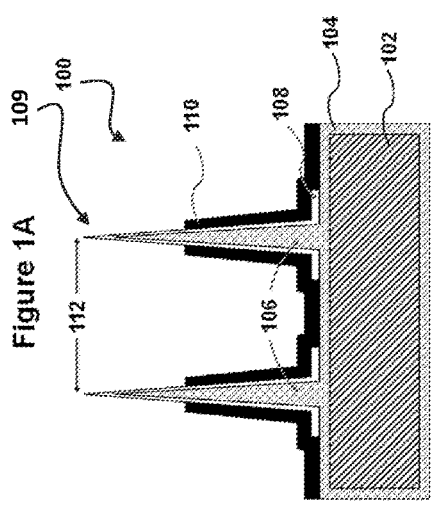

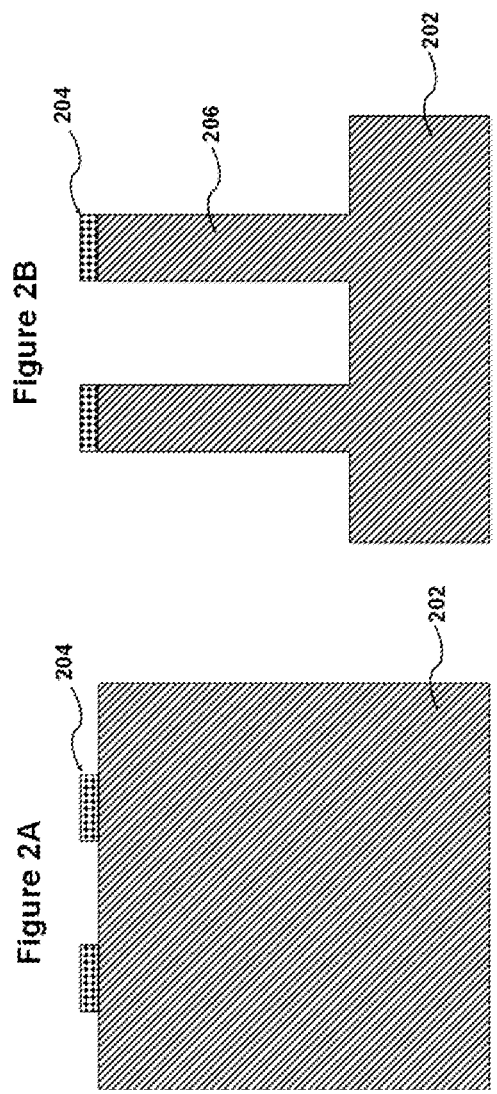

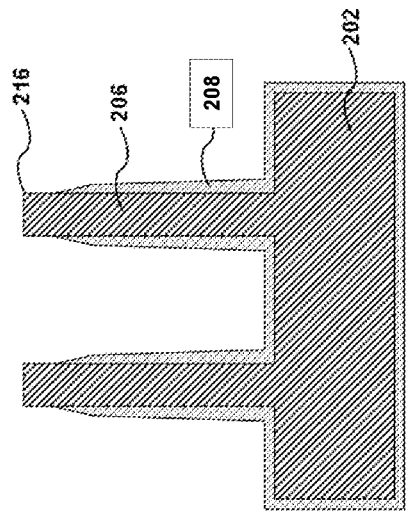
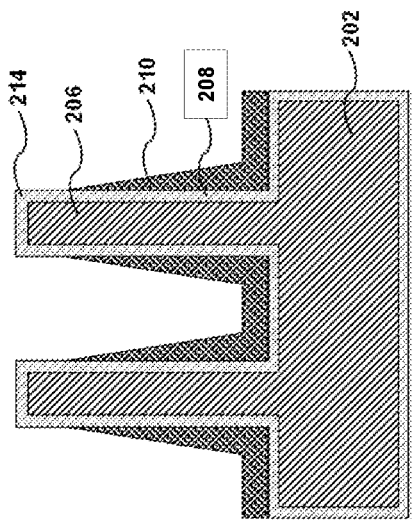

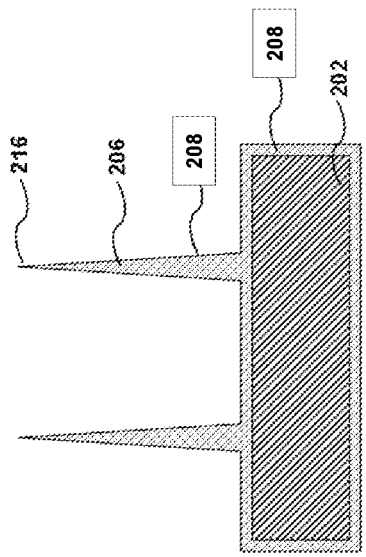
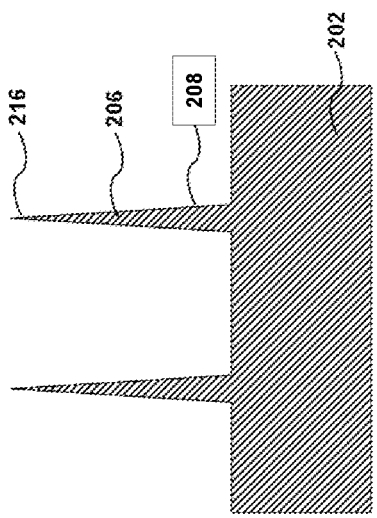

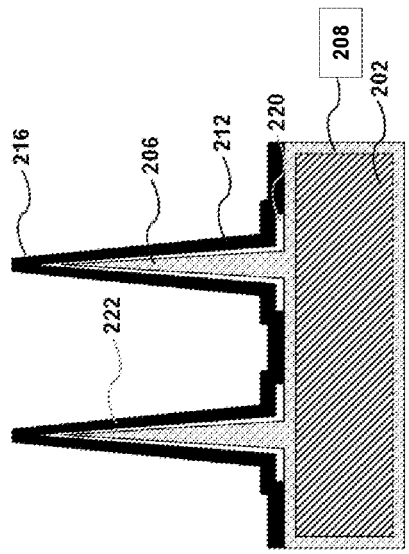
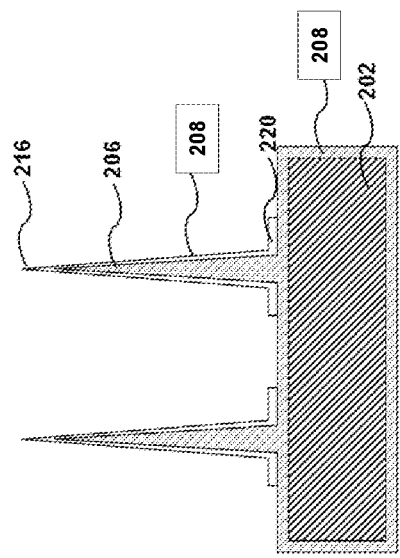

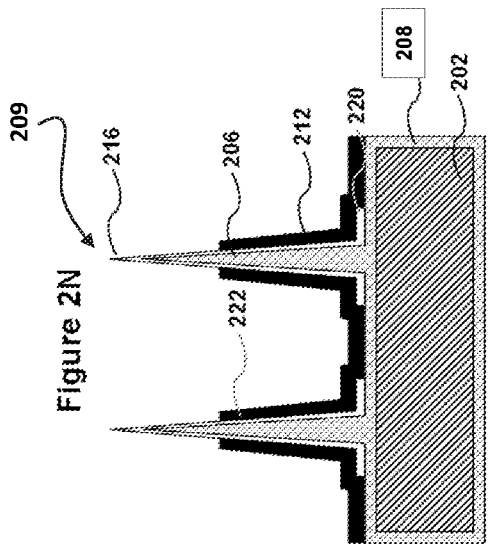
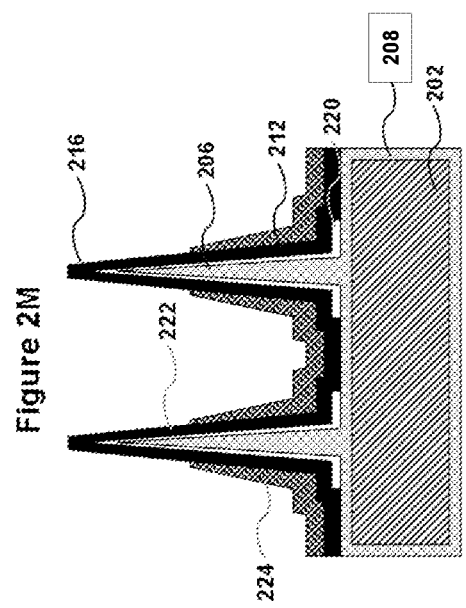

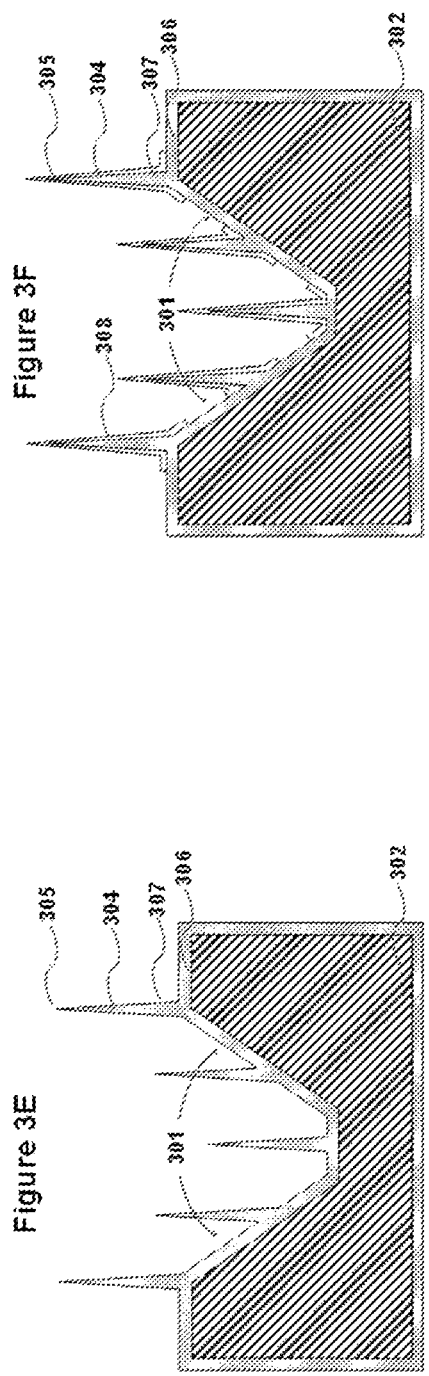

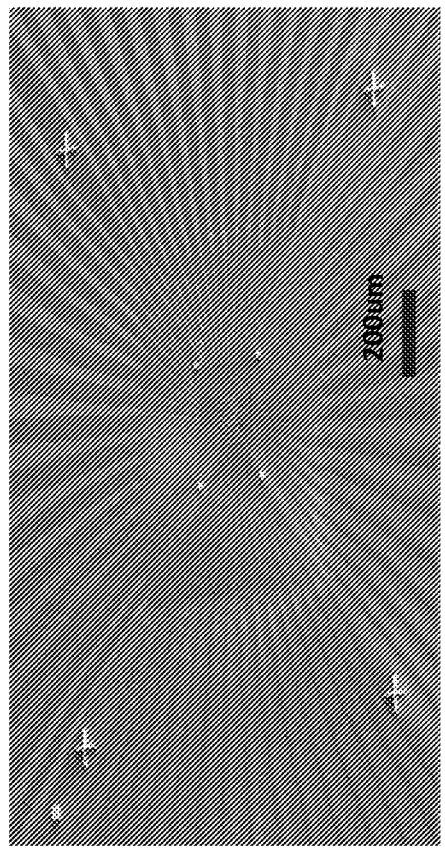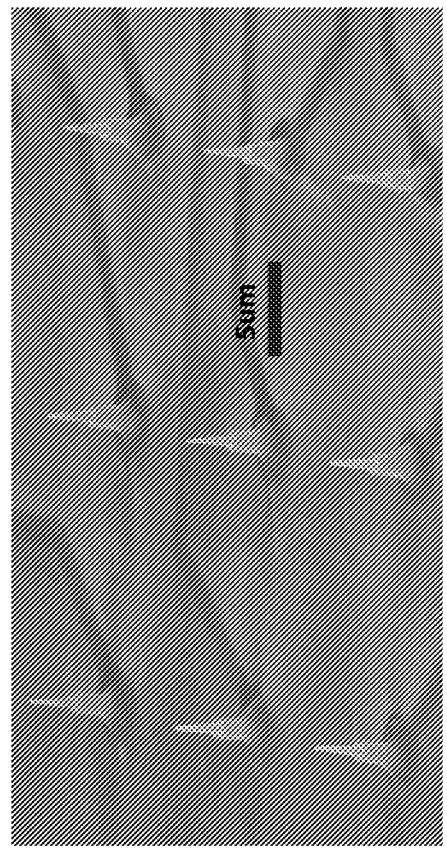
Figure 5A
Figure 5B

SHARP, VERTICALLY ALIGNED NANOWIRE ELECTRODE ARRAYS, HIGH-YIELD FABRICATION AND INTRACELLULAR RECORDING

PRIORITY CLAIM AND REFERENCE TO RELATED APPLICATION

The application claims priority under 35 U.S.C. § 119 and all applicable statutes and treaties from prior provisional application Ser. No. 62/669,639, which was filed May 10, 2018.

FIELD

Fields of the invention include nanowire electrode arrays (NEAs) and intracellular potential measurement, and drug screening with 3D tissue and mini-organoids. Other applications for NEAs of the invention include to field-emission devices, light, ion, and particle detectors, etc.

BACKGROUND

The recording of minute potential fluctuations and ionic currents of individual cells in large populations of excitable cells such as neurons, cardiomyocytes, and muscle cells is important for the evaluation of the healthy and diseased function of excitable cells and the screening of suitable drugs that can help mitigate the dysfunction in brain, heart, and muscle diseases. In biological and clinical research, patch-clamp is the gold-standard and most widely used and efficient technique to probe the dynamic potential fluctuations and ion-gate current exchanges in excitable cells. [1] However, patch-clamp is quite invasive and doesn't meet the need to scale to large densities, long term, and intracellular electrophysiological intervention. While Microelectrode arrays (MEAs) enable long-term recordings from networks of neurons, they measure extracellular potentials and therefore lack the sensitivity to subthreshold potential oscillations that are important features for drug screening.

Penetrating electrodes have been developed as excitable cell sensors, with different structures, such as Pt nanopillars [Xie, C., Lin, Z., Hanson, L., Cui Y. and Cui, B., Intracellular recording of action potentials by nanopillar electroporation, Nature Nanotechnology 2012 7, 185-190], $IrO_2$ nanotubes [Lin, Z. C., Xie, C., Osakada, Y., Cui, Y. and B. Cui, B., Iridium Oxide Nanotube Electrodes for Sensitive and Prolonged Intracellular Measurement of Action Potentials, Nature Communication 2013 5, 3206], and $IrO_2$ nanowires [U.S. Pat. No. 7,905,013: Method for forming an iridium oxide (IrOx) nanowire neural sensor array]. Those NEAs were achieved with pre-defined contact leads on the substrate followed by selective growth of nanowires on the designed electrodes. However, their tip diameter is large and for intracellular recording, they require electroporation, the application of an electric field larger than the breakdown field of the cell membrane. Additionally, they are not individually addressable, and in some cases such as for the Pt nanorods, they are fabricated with a serial process of focused ion beam deposition. The $IrO_2$ nanowires are vulnerable to delamination failure of electrodes due to the poor mechanical integrity and additionally suffer from the aforementioned size shortcomings.

Prior Background Publications

1. Hodgkin, A. L., and Huxley, A. F., Action Potentials Recorded from Inside a Nerve Fibre, Nature 1939 144, 710-711

2. Xie, C., Lin, Z., Hanson, L., Cui Y. and Cui, B., Intracellular recording of action potentials by nanopillar electroporation, Nature Nanotechnology 2012 7, 185-190

3. Lin, Z. C., Xie, C., Osakada, Y., Cui, Y. and B. Cui, B., Iridium Oxide Nanotube Electrodes for Sensitive and Prolonged Intracellular Measurement of Action Potentials, Nature Communication 2013 5, 3206

4. U.S. Pat. No. 7,905,013: Method for forming an iridium oxide (IrOx) nanowire neural sensor array 5. Liu, R., Chen, R., Elthakeb, A. T., Lee, S. H., Hinckley, S., Khraiche, M. L., Scott, J., Pre, D., Hwang, Y., Tanaka, A., Ro, Y. G., Matsushita, A. K., Dai, X., Soci, C., Biesmans, S., James, A., Nogan, J., Jungjohann, K. L., Pete, D. P., Webb, D. B., Zou, Y., Bang, A. G., and Dayeh, S. A., High Density Individually Addressable Nanowire Arrays Record Intracellular Activity from Primary Rodent and Human Stem Cell Derived Neurons, Nano Lett. 2017, 17(5), 2757-2764

6. Werner, M., Blanquer, S. B. G., Haimi, S. P., Korous, G., Dunlop, J. W. C., Duda, G. N., Grijpma, D. W., and Petersen, A., Surface Curvature Differentially Regulates Stem Cell Migration and Differentiation via Altered Attachment Morphology and Nuclear Deformation, Adv. Sci. 2017, 4, 1600347

7. Kim, D. H., Lipke, E. A., Kim, P., Cheong, R., Thompson, S., Delannoy, M., Suh, K. Y., Tung, L., and Levchenko, A., Nanoscale cues regulate the structure and function of macroscopic cardiac tissue constructs, PNAS 2010, 107.2, 565-570.

Recent Developments

Dayeh et al. US Published Patent Application No. US20170231518 discloses conformal penetrating multi electrode arrays. A plurality of penetrating semiconductor micro electrodes extend away from a surface of a flexible substrate and are stiff enough to penetrate cortical tissue. Electrode lines are encapsulated at least partially within the flexible substrate and electrically connected to the plurality of penetrating microelectrodes. The penetrating semiconductor electrodes can include pointed metal tips. The pointed metal tips are formed by some consumption of silicon during an etching process and coating with metal. The pointed metal tips are micrometer scale in diameter (much greater than 100 nm in diameter) and hundreds of micrometers long to penetrate the brain to the right cortical area. These electrodes measure extracellular activity from intact brains, and even in the depth of mini-brains, but cannot measure intracellular activity.

SUMMARY OF THE INVENTION

A preferred embodiment is nanowire electrode array comprising a plurality of vertical nanowires extending from a substrate, each of the nanowires comprising a core of unitary first dielectric material that also covers the substrate and is unitary with the substrate, each core having a sharp sub-100 nm diameter tip and a wider base, electrode leads on sidewalls to the tip of the nanowire, and second dielectric covering the electrode leads. The substrate can include a window for simultaneous optical imaging and electrophysiological recording.

An embodiment is a method for forming a nanowire electrode array comprising a plurality of vertical nanowires extending from a substrate. The method includes etching a substrate in a pattern that forms vertical cores of material extending away from remaining unetched portions of the substrate. Another step includes thinning and converting the vertical cores and a surface of the substrate into first dielectric. Electrode leads are formed to tips of the vertical cores. The electrode leads are protected on a base portion of the vertical cores with second dielectric while leaving the electrode leads exposed at a tip portion of the vertical cores.

BRIEF DESCRIPTION OF THE DRAWINGS

FIG. 1A is a schematic cross-section diagram of a preferred embodiment nanowire electrode array of the invention; FIG. 1B is a perspective view of the array; FIG. 1C is a top view of the array;

FIGS. 3A-3G are schematic cross-sectional diagrams illustrating a preferred method for fabricating a nanowire electrode array on a shaped surface;

FIGS. 5A-5D are images at different magnifications of an experimental nanowire electrode array.

DETAILED DESCRIPTION OF THE PREFERRED EMBODIMENTS

Figure 2C:
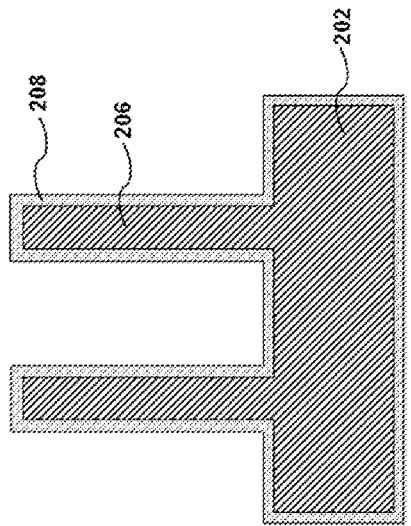
FIGS. 2A-2N are schematic cross-sectional diagrams illustrating a preferred method for fabricating a nanowire electrode array in accordance with FIGS. 1A-1C.

A preferred nanowire electrode array of the invention includes nanowire electrodes projecting from a surface. Electrode leads are preferably individually connected to nanowire electrodes in the array. Each electrode includes sharp tip and a wider base. Electrode leads extend on the nanowire sidewalls to near the tip of the nanowire. Dielectric on the sidewalls covers the electrode leads. The tips are ultra-sharp, sub 100 nm, preferably less than 20 nm, more preferably less than 10 nm and most preferably a few nm in diameter at the tip. The tips in an array of the invention can therefore penetrate individual cells in cell culture, such as a mini-brain culture. Intracellular recording is typically achieved with one electrode per cell. However, even if multiple nanowire electrodes are used per one cell, they would ideally show identical intracellular signals. The nanowire electrode to electrode spacings are typically controlled between 0.75 to 20 μm, and, depending on the applications, much larger spacing up to a few mm is possible. Considering that the cell body of a neuron is 5-10 μm, arrays can be fabricated with a spacing to control a single or multiple nanowire electrodes are placed in cell body. A substrate that provides the surface can include a window on the back side for simultaneous optical imaging and electrophysiological recording.

The present invention provides methods for fabrication of a nanowire electrode array that can minimize the electrode tip to a size suitable for natural internalization of cell membranes i.e. intracellular probe, and is scalable to integrate thousands of channels (1 nanowire comprise 1 channel) in one platform. A preferred method provides fabrication of high yield nanowire electrode arrays (NEAs) with ultra-sharp tips on 2-dimensional (2D) and 3-dimensional (3D) surfaces, as well as on transparent windows in backetched substrates for simultaneous optical imaging and electrophysiological recording. A preferred method uses the NEAs to record intracellular potentials and currents from excitable cells. Other embodiments include NEAs in field-emission devices and employed as detectors, such as light, ion, and/or particle detectors, etc.

Individual steps in a preferred method of the invention include standard silicon microfabrication techniques combined with nanolithography techniques that create biocompatible conductive nanowire arrays, that are individually electrically addressable. Selective oxidation and wet etching of a preferred method provides vertically tapered nanowires. Repeated thermal oxidation and wet etching further reduces the nanowire diameter at the nanowire tips. This process results in a larger diameter at the base of the nanowire to provide mechanically stability and small diameter at the nanowire top with sharp tips that can be as small as a few nanometers in diameter to naturally permeate cell membranes. Preferred fabrication methods make minimal use of metallic layers and promise excellent biocompatibility. Methods of the invention can result in the fabrication of nanowires on planar surfaces (2D) and shaped 3D surfaces, such as angled and curved surfaces.

Such sharp tips can penetrate into excitable cell membranes, such as neurons, cardiomyocytes, other muscle cells, etc., for in-vitro intracellular recordings of the cell potential and ionic currents. NEAs of the invention can provide multiple intracellular measurements per a single cell (with multiple nanowires that are closely spaced simultaneously permeate one cell membrane) or intracellular measurements from a large network of excitable cells.

Advantages of fabrication methods of the invention include high yield and process robustness. NEAs of the invention can provide low impendence, high density, high sensitivity, high aspect ratios, individual addressability, minimal invasiveness and biocompatibility, high probability for cell viability during measurement, attachment and extended network growth for 2D cardiomyocyte syncytia or 3D tissue like structures and organoids. In addition, tissue slices and organoids can be applied to the platform and intracellular electrophysiological recordings can be performed. Preferred NEA nanowire sensors of the invention advance the state of the art for excitable cell signal recording and stimulation and for longitudinal measurements of cell potentials and ionic currents important for drug screening.

Preferred embodiment NEAs include sharp nanowire tips with a diameter as small as sub-10 nanometers, down to a few nanometers, which provides for cell membrane penetration for intracellular electrophysiology while being minimally invasive. Via preferred fabrication methods a selective etch of nanowire tips and different thermal oxidation rates of the tip and base portion of nanowires enable $SiO_2$ tips as sharp as 4 nm in diameter and slightly larger diameter when coated with metal, which is suitable for intracellular recording, stimulation or inhibition of excitable cell's activities at single cellular resolution. Such ultra-sharp tips easily penetrate into cell membranes, and a relatively large nanowire base promotes the formation of excellent seal between the nanowire and the cell, which is expected to preserve the cell's health and its long-time activity and survivability for longitudinal intracellular electrophysiological experiments. While silicon was used as a substrate, and is preferred, other materials that can be oxidized and processed to form sharp tips of unitary oxide can be used to form nanowire sensor arrays of the invention. For example, Ge can be oxidized to form $GeO_2$.

Preferred embodiment NEAs can be provided with an adjustable height from a few μm to a few 10 s μm providing a high aspect ratio, e.g. ~500. The nanowire surface can be coated with a biocompatibile conductive layer, such as Au, Pt, $IrO_2$, PEDOT:PSS, Ag/AgCl, without restrictions in order to lower its impendence and enhance its electrochemical interaction with the excitable cell.

Preferred embodiment NEAs provide both high density and individual addressability. Commercial fabrication equipment and optimization can and has been used to further reduce the center-to-center spacing of 750 nm, though such super high density may not be required. Preferred center to center spacings range from 5-40 μm. The individual addressability enables each vertical nanowire to serve as a single channel/electrode for electrophysiological intervention. The ultra-scaled and highly compact NEAs can record action potentials in each local position at synapses, somas, dendritic and axonal peripheries during neuronal activities, for example. The combination of high density and individual addressability enables recording action such as potential generation and propagation in a single cell or cellular networks, and can extend longitudinal intracellular recordings from tissues and organoids, including primary and pluripotent induced stem cells, and from tissue slices.

Preferred embodiment NEA fabrication methods are flexible in terms of layout design. Layouts can be engineered to meet different recording requirements, because methods of the invention can provide various densities and areal registration/location.

Preferred embodiment NEA fabrication methods provide high-yield fabrication and the produced NEAs are robust. Experiments demonstrated near 100% yield. Preferred methods use electron-beam or nano-imprint lithography, have very high yield (nearly 100% in all batches). The vertical nanowires are mechanically robust and do not fall down with sample handling and long-distance shipping.

Preferred embodiment NEAs provide for a high probability of cell viability, attachment and healthy growth: A preferred NEA upon a shaped surface mimics the native 3D extracellular environment of cells in the animal/human body, which highly improves the probability for cell viability, attachment and healthy growth. Different 3D curvature surfaces can apply different forces on the cell, which can influence cell development and enhanced tissue regeneration.

Preferred embodiments of the invention will now be discussed with respect to the drawings and experiments used to demonstrate the invention. The drawings may include schematic representations, which will be understood by artisans in view of the general knowledge in the art and the description that follows. Features may be exaggerated in the drawings for emphasis, and features may not be to scale.

FIG. 1A is a partial cross-sectional view of a preferred nanowire sensor array of the invention. The nanowire sensor array 100 is supported by a substrate of Si 102. A dielectric layer of $SiO_2$ 104 covers the substrate 102, is unitary with the substrate 104 (having been converted from material of the substrate) and is also unitary with the cores 106 of nanowire electrodes, which cores 106 are formed unitarily with the dielectric layer 104 that covers the substrate 102, and that was converted from the material of the substrate. Because the cores 106 of nanowire probes can be thermally oxidized together with the substrate as a single entity, the mechanical strength of the nanowire probes is tolerant to sample movement and shipping and to cell micromotion for the duration (>1 week) of a typical experiment that includes a cell culture. A conductive layer 108, e.g. Au, Pt, $IrO_2$, PEDOT:PSS, Ag/AgCl, etc. is coated uniformly on the sidewall of the dielectric cores 106 and forms the electrode leads for each complete nanowire electrode 109. A second dielectric layer 110, e.g. $SiO_2$, $SiN_x$, etc. passivates the device surface, but does not extend to the distal end of probe tip.

The cores 106 after being coated with the conductive layer 108 to form the nanowire electrodes 109 have a diameter of a few to ~60 nm, with tips of preferably less than 20 nm, preferably less than 10 nm and most preferably a few nm, and a height of 2 μm~15 μm depending on the type of cell-culture and tissue application requirements. The electrode center-to-center spacing 112 can vary from sub-micron to tens of microns according to the desired experimental requirements, tissue coverage, and total channel count for a given platform. The conductive layer 108 has a thickness of ~10 nm-100 nm. In preferred embodiments, the metal layers are deposited inside a high-vacuum chamber, and, in this system, metal particles are showered on the sample in a vertical direction. Even if the metal layers are deposited ~10 nm-100 nm on the substrate, the metal layers on the nanowire can be limited to a deposit of only a few nanometers.

FIG. 1B and FIG. 1C illustrate how each nanowire electrode 109 is electrically conducted from nanowire tip 121, to sidewall metal layers 122, metal leads 123, and peripheral metal pads 124. Preferably, half to three-quarters of the nanowire height is passivated with the additional dielectric 110, which permits an exclusive measurement of intracellular potentials without exposure to extracellular potentials. The measurement is only taken from the metal tip region of the nanowire probe. Metal leads 123 are also covered by the dielectric passivation layer 110 to prevent the signal cross-talk between adjacent electrodes. The metal connections, 121, 122, 123, and 124 can be patterned by photolithography, electron beam lithography (EBL), shadow or nanoimprint lithography depending on their feature size.

FIG. 2 illustrates a preferred fabrication method. In FIG. 2A, an etching mask 204 is patterned on top of Si 202. The etching mask 204 can be metal, e.g. Ni, Hydrogen Silsesquioxane (HSQ), photoresist, etc. and can be patterned by EBL or photolithography according to the requirements of the electrode diameter and height. Then, the vertical nanowires are fabricated by a masked dry etching process, as shown in FIG. 2B. A reactive ion etching (RIE) and inductively coupled plasma (ICP) based etching process then follows to remove all the Si except for the area underneath the etching mask 204, so that Si material to be converted in later steps to $SiO_2$ for each vertical neural probe core 206 is supported by and is unitary with the substrate Si 202, which is left by the etching process. The epitaxial structure evolving from the unitary substrate to the etched nanowire provides higher mechanical stability than hybrid multi-material platforms, such as those bonded to or deposited/grown on the surface of the substrate.

The etching mask 204 can withstand the dry etching process, and each etched electrode core material 206 can be formed (after dielectric conversion and thinning described below) to have a diameter from ~1 nm-60 nm and a height generally in between 2 μm~15 μm. The diameter of the vertical electrode core material 206 is defined by the starting diameter of the etching mask 204, and the height is determined by the ICP/RIE etching process time. When the desired height of the nanowire is achieved, the etching mask is removed as shown in FIG. 2C. Depending on the material used as an etching mask, the relevant etcher/remover is required. For example, if the etching mask was Ni, a Ni etchant such as diluted nitric acid is used, and if the etching mask was HSQ, a buffered oxide etch (BOE) is used.

Figure 2D:
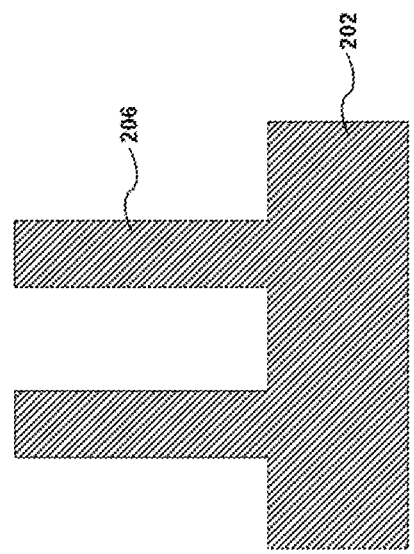
Figure 2H:
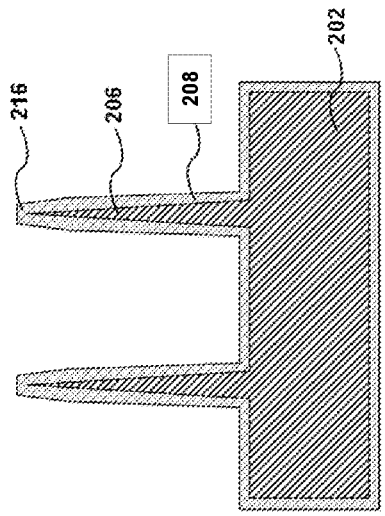
Figure 2G:
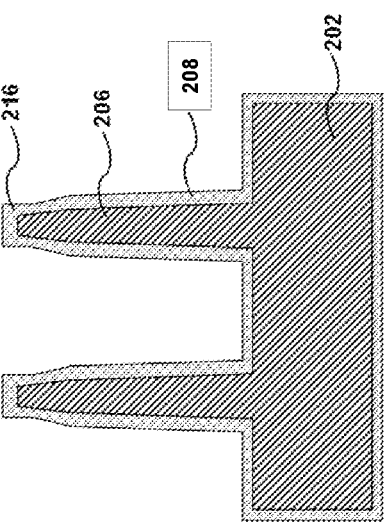

FIGS. 2D to 2J show steps for nanowire thinning to obtain sharp tips from the core material 206. In FIG. 2D etched vertical core material 206 is thermally oxidized with a dielectric layer of $SiO_2$ 208. Following a spin coating of a polymer layer 210 and $O_2$ plasma etching as shown in FIG. 2E, the base of dielectric layer 212 is protected and the tip region 214 is exposed for wet etching. The resulting structure is shown in FIG. 2F, where the dielectric layer 208 covers the whole surface area and exposes the distal tip 216 of each core starting material 206, enabling the faster thermal oxidation rate in the tip 216 then that in the base region 214 as shown in FIG. 2G. During wet etching of the surface $SiO_2$ layers, the nanowires become thinner, as shown in FIG. 2H, their surface smoother, and their tips sharper. By repeating the steps in FIG. 2H, a nanowire morphology with a very sharp tip is obtained as depicted in FIG. 2I. With the last step of thermal oxidation, a thick dielectric layer, from 400 nm to 2 µm, is formed on the surface, as shown in FIG. 2J. All the nanowire cores 206 from tip 216 to base 212 have then been converted to $SiO_2$ and thinned to have ultra-sharp tips. This $SiO_2$ of the cores is unitary with the thick $SiO_2$ 208 formed on the substrate 202, which is also unitary with the substrate 202. The unitary nature of the pure $SiO_2$ cores 206 provides advantages such as natural covalent bonds formed through the reaction of $O_2$ with Si to form the nanowire and the interface with the substrate and resultant mechanical stability. Additionally, a single and high quality thermal oxide layer that serves the purpose of electrical isolation throughout the surface of the platform including the nanowire and the planar substrate surface in between, is obtained.

A thin (5 nm-50 nm) conductive layer 220, e.g. Au, Pt, $IrO_2$, PEDOT:PSS, Ag/AgCl, etc., is uniformly coated on the nanowires to form a conductive layer and connect the electrode tip, that will be present inside the cell, as shown in FIG. 2K, where the nanowire makes contact with the intracellular medium of the cell and the electrochemical potential and/or current are being recorded, to the interconnect pad to the measurement system. The size of nanowire tip will be slightly increased according to the deposited thickness and method of deposition of the conductive layer. Atomic layer deposition can provide the thinnest layers (1-5 nm) and therefore smallest expected tip diameters (2-6 nm).

In the FIG. 2L, vertical electrodes 206 are passivated with a thin dielectric layer 222, which thickness of usually 200 nm-500 nm, to prevent electrochemical interaction with the electrode leads for several weeks and to reduce the signal cross-talk between adjacent electrodes. Following a spin coating of polymer layer 224 and $O_2$ plasma etching to etch the top-most and thinnest parts of the polymer layer 224 as shown in FIG. 2M, the base of dielectric layer 212 is protected and the tip area 216 is exposed for wet etching. The spin coated polymer layer 224 is very thin near the nanowire tips, but thick on the substrate. A short oxygen plasma etching results in selective exposure of nanowire tips while polymer 224 remains elsewhere. Following wet etching of the dielectric layer on the exposed region of the tip and after removing the polymer layer, the final device with completed nanowire electrodes 209 is depicted in FIG. 2N. The dielectric layer 222 covers the whole area of the metal connection, but exposes the tip 216 of each vertical electrode 209, enabling the signal recording from each vertical electrode 209 while ruling out the noise and current from underneath metal connections.

The NEA sensor platform can also be formed on non-planar surfaces. The method to fabricate the NEA sensor platform on 3D surfaces is similar to the method of fabrication on planer surfaces. The main difference is that a shaped surface is fabricated prior to the fabrication of the NEAs. A preferred method for forming a nanowire electrode array includes deposition of a masking layer consisting of discs with diameters of tens of nanometers to a micrometer in a groove where the diameter is changed from the highest point of the groove to the lower point to provide a controlled single nanowire diameter and etching of the nanowires on the groove to create nanowire tips at different heights within the groove.

Figure 3B:
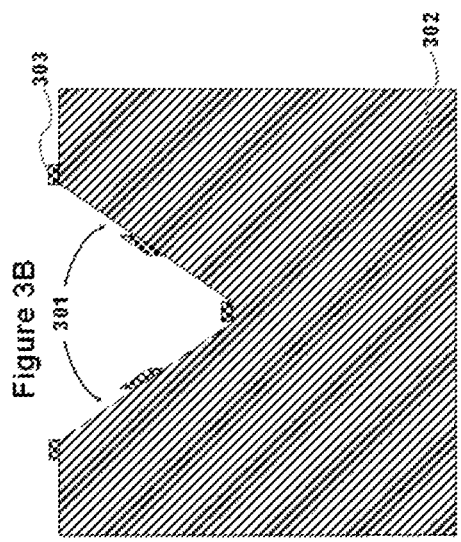
Figure 3A:
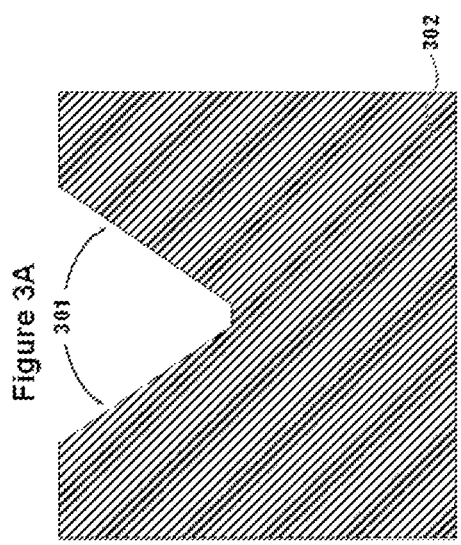
Figure 3D:
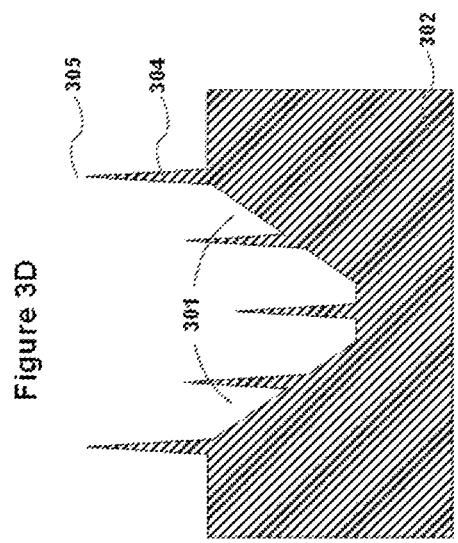
Figure 3C:
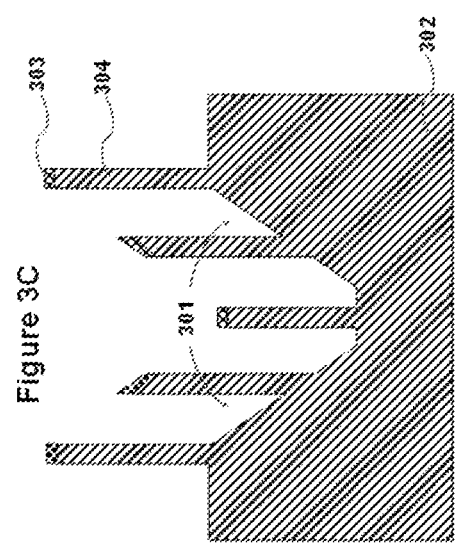

In FIG. 3A, a shaped surface 301, which can be V-shape, groove, round convex, round concave, rough surface, or any other curved surface, is fabricated in an Si substrate 302. A V-shape surface as shown as an example, and can be formed by KOH solution etching for Si. The etching mask 303 is patterned on top of the shaped surface 301, as shown in FIG. 3B Similarly to fabrication on a planar surface, the etching mask 303 can be metal, e.g. Ni, Hydrogen Silsesquioxane (HSQ), photoresist, etc. and can be patterned by EBL or photolithography according to the requirements of the electrode's diameter and height. Then, the vertical nanowires 304 on shaped surface 301 are fabricated by a masked dry etching process based on RIE and ICP, as shown in FIGS. 3C. The etching mask 303 can stand the dry etching process, and the etched probe 304 has a tip diameter from ~1 nm-60 nm and a height generally in between 2 µm~15 µm Similar to fabrication steps of in FIG. 2C to 2J, the etching mask is removed, repeated thermal oxidation and selective etching are proceeded until we obtain the final probe morphology with a very sharp tip 305 as depicted in FIG. 3D. With the last step of thermal oxidation, a thick dielectric layer, from 400 nm to 2 µm, is formed on the surface 306, as shown in FIG. 3E. All the probes 304 from tip 305 to base 307 are composed of $SiO_2$. Also, as shown in FIG. 3F, a conductive layer 308, e.g. Au, Pt, $IrO_2$, PEDOT:PSS, Ag/AgCl, etc., is uniformly coated on the nanowire on the sloped surface to form a conductive layer and connect the electrode tip, that is intended to penetrate the cell membrane, to the pad, where the nanowire makes contact with the intracellular medium of the cell and the electrochemical potential and/or current are being recorded. In FIG. 3G, the vertical electrodes 304 are passivated with a thin dielectric layer 309, which thickness of usually 500 nm, to prevent electrochemical interaction with the electrode leads and minimize the signal cross-talk between adjacent electrodes Similar to the method of fabrication on planar surfaces, following a spin coating of a polymer layer 309 and $O_2$ plasma etching, the base of dielectric layer 307 is protected and the tip area 305 is exposed for wet etching. Following wet etching of the dielectric layer on the exposed region of the tip and after removing the polymer layer, the final device is depicted in FIG. 3G.

While the substrates in the above examples were planar and the nanowires were formed on one "side" of the substrates, non-planar surfaces can be processed in the same way. For example, the nanowires could be formed on curved and slanted surfaces to provide a 3D distribution of the nanowires to sample electrophysiological activity at multiple layers in 3D tissue and mini-organoids.

Figure 3H:
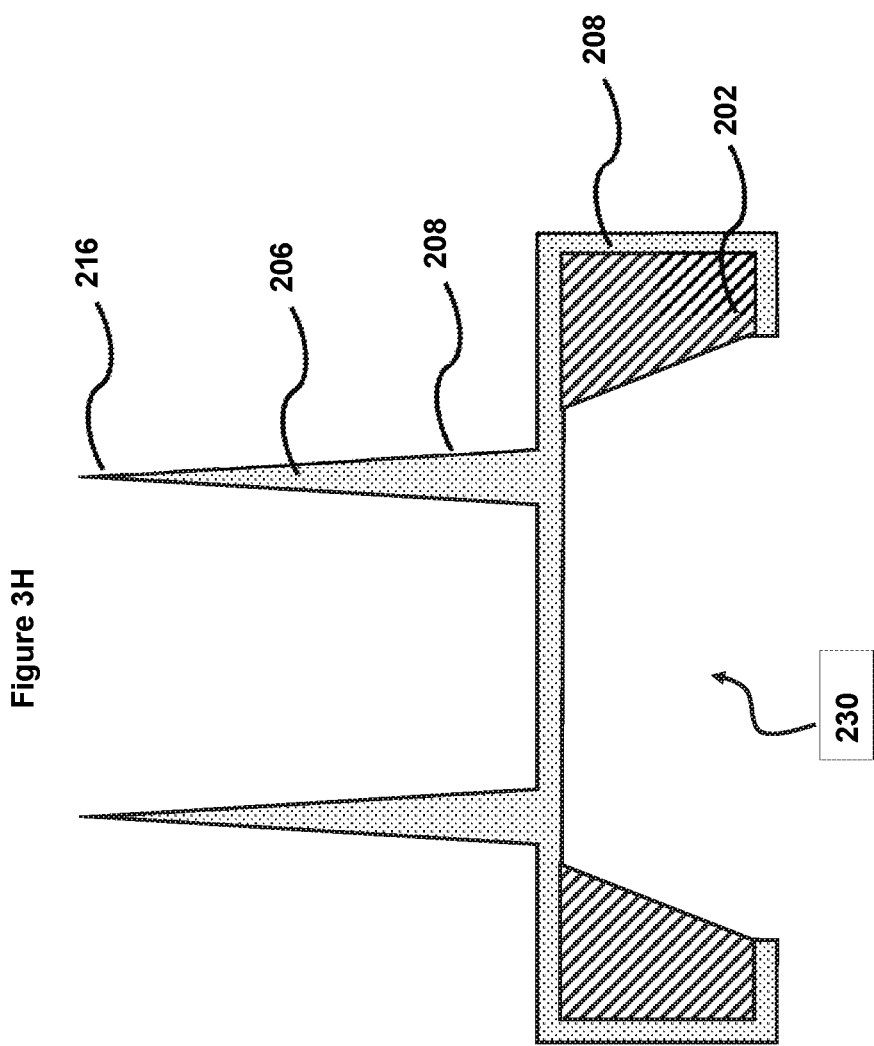
FIGS. 3H-3I are schematic cross-sectional diagrams illustrating a preferred method for fabricating a transparent nanowire electrode array platform with a window for optical imaging.
Figure 3I:
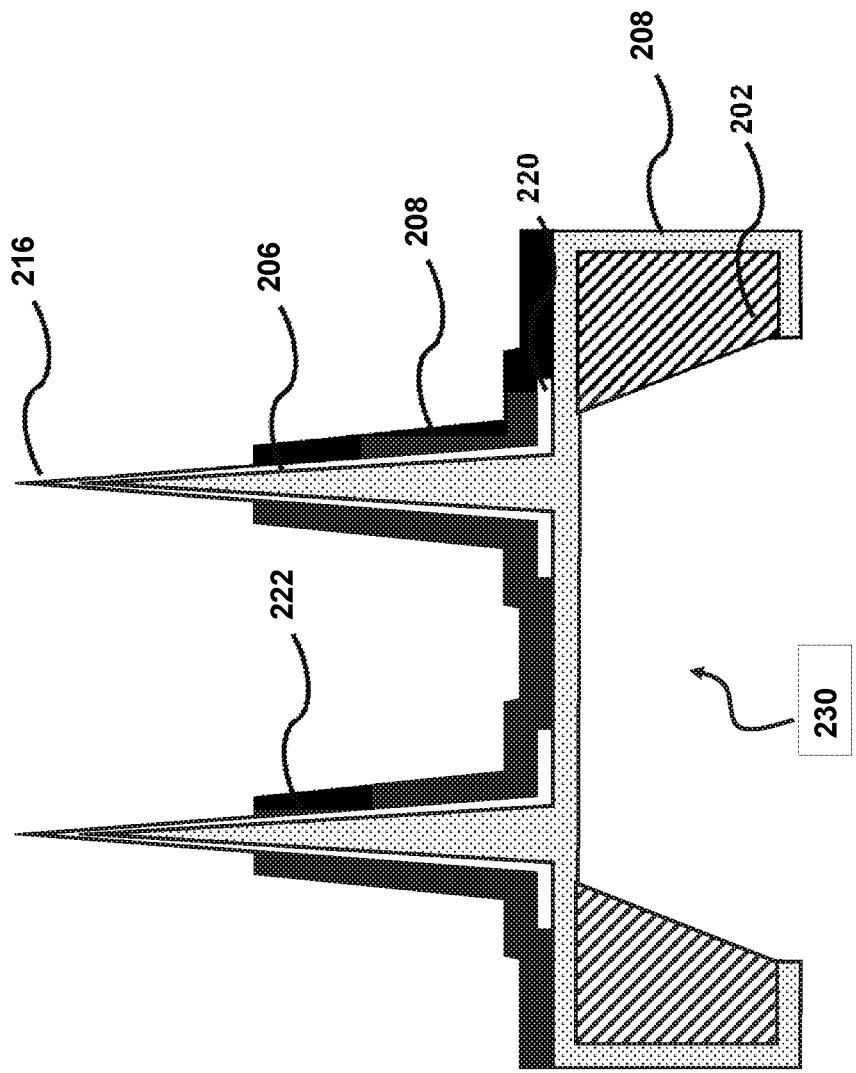

Simultaneous optical and electrophysiological recording of cell activities is advantageous. A transparent NEA platform can be fabricated by adding one fabrication step between FIGS. 2J and 2K and keeping all the other fabrication processes of planar NEA the same. FIG. 3H shows the formation of a transparent window 230 in a Si wafer using anisotropic wet etching process. After completing the nanowire oxidation process described in FIG. 2J, $SiO_2$ layers 218 formed on the backside of the Si wafer 202 are patterned by typical lithography and dry-etching steps to have square-shaped openings with an area ranging from 200 by 200 µm$^2$ to 2000 by 2000 μm². Then, tetramethylammonium hydroxide (TMAH) solution that has good etch selectivity to Si over $SiO_2$ is used to selectively etch the Si wafer 202 through the $SiO_2$ etch mask 218, opening a transparent window 230 below the nanowire array 206 as shown in FIG. 3H. For thick Si wafers, Si wafer can be first thinned down by dry etching and TMAH could be used to remove the remaining Si layer below the nanowire array 206. After making the transparent window 230 in Si wafer 202, the same processes described in FIG. 2K-2N can be used, which would result in a transparent NEA platform as shown in FIG. 3I.

Figure 4:
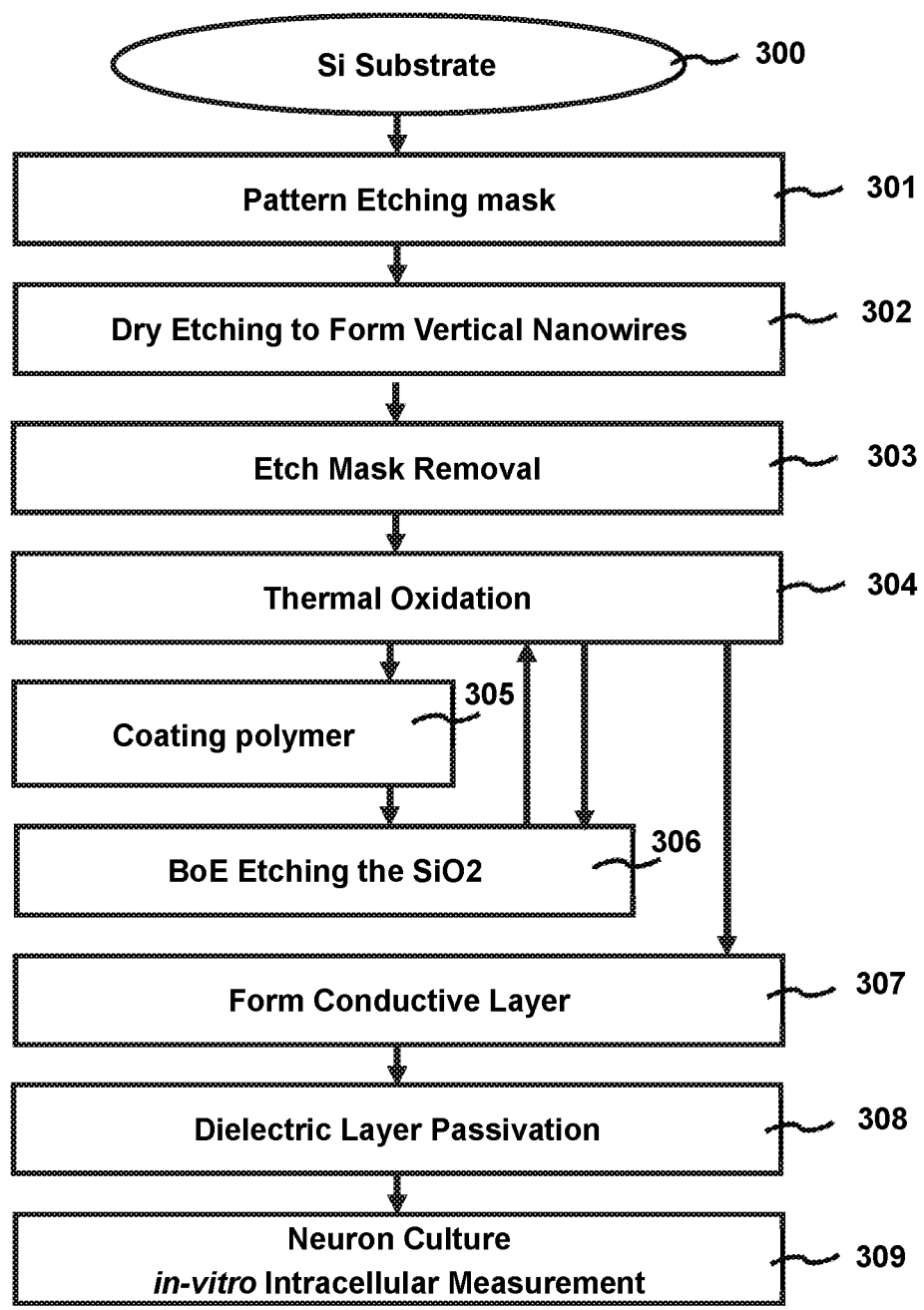
FIG. 4 is a flowchart of a preferred method for fabricating a nanowire electrode array.
Figure 5C:
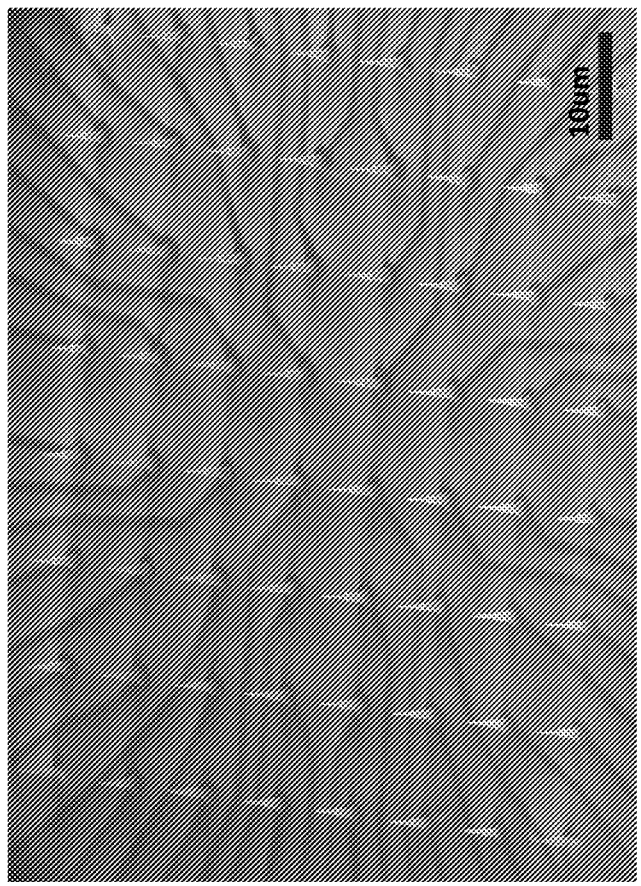
Figure 5D:
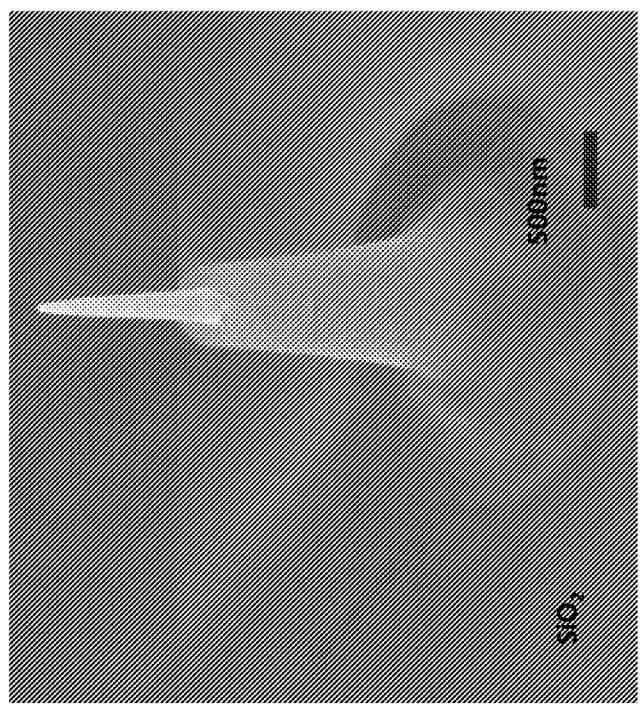

FIG. 4 illustrates the overall flow of preferred fabrication methods. The NEA platform can be made on the planar surface (2D), starting from step 402 that electrode etching mask patterned on Si substrate 400, and shaped surface (3D), starting from step 401 that shaped surface is patterned and formed in the Si substrate 400, following by patterning the probe etching mask. Then the dry etching 403 is performed to form the vertical nanowires on 2D or 3D surface, and etch-mask removal 404, thermal oxidation 405, polymer coating 406 and $SiO_2$ etching 407 follows. Then the thermal oxidation step is repeated 405 followed by $SiO_2$ etch 407 for several times to thin the nanowire tip diameter. Conductive layer 408 from vertical nanowire tip to interconnect pads are formed by lithography and metal deposition. Dielectric Layer Passivation 409, polymer coating and tip dielectric layer etch are performed.

In the experiments, dot etch masks and alignment marks were patterned on

Si by utilizing EBL and metal deposition of a 220 nm thick Ni layer. Following an ICP/RIE etching process to fabricate the nanowires atop the Si substrate, and the resulting nanowire height was ~10 μm. A large flexibility in the design and fabrication of various NEA layouts can be achieved by utilizing EBL to pattern the etch mask dots and the electrode leads and pads. Ni dots were removed by diluted nitric acid. A thermal oxidation step at 1100° C. then followed to form ~200 nm thick $SiO_2$ surface layer including the sidewall of nanowire. Then, PMMA was spun coated on the device surface, introducing a uniform thickness ~300 nm covering the flat surface of device, while a graded thinner layer covered the sidewall at the base of each vertical nanowire toward its tip where PMMA is thinnest. A short $O_2$ plasma step was introduced to etch/react with all the PMMA at the tip of each vertical nanowire, and a buffered oxide etch (BOE) was used to etch the exposed $SiO_2$ layer at the tip region. Finally, all the PMMA residuals were removed by acetone and $O_2$ plasma. In the following step of thermal oxidation, and because the tip was not covered with $SiO_2$ while the base of the vertical nanowire was covered with $SiO_2$, the thermal oxidation rate is faster at the tip than at the base of the nanowire. BOE etching was followed to thin down the nanowire and get a tapered nanowire shape. Thermal and BOE etching is repeated for several times until a very sharp tip of a few nanometers in diameter is achieved. Then, the last step of thermal oxidation was performed in order to oxidize and isolate these nanowires and the whole substrate surface. EBL of center electrodes and 3D conformal metal deposition of 30 nm Ti/100 nm Au were performed. Photolithography of the outer electrode leads and pads and metal deposition were then performed. Before the in-vitro measurement, the 3D electrodes were passivated with a PECVD $SiO_2$ layer. The 1D NEAs were passivated by the dielectric layer at the base and the sidewall while with the tip was exposed for direct interactions with intracellular medium. 200 nm $SiO_2$ was first deposited all over the substrate by PECVD. A layer of PMMA was then spun coated atop the surface and the topmost layers were removed by $O_2$ plasma to remove PMMA at the nanowire tip followed by BOE dip to etch the exposed PECVD $SiO_2$ on the tip of the nanowire and the etch stops at the underlying metal layer. Then, we removed the PMMA by acetone and $O_2$ plasma and the fabrication process of the vertical nanowire probe array was therefore completed.

FIGS. 5A-5D provide SEM images of an example fabricated NEA of the invention. (a) overview of the sensor, (b) overview of 60 individually addressable nanowire channels, (c) local position of 3*3 array, and (d) overview of a single nanowire electrode/channel While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. A nanowire electrode array comprising a plurality of vertical nanowires extending from a substrate, each of the nanowires comprising a core of unitary first dielectric material that also covers the substrate and is unitary with the substrate, each core having a sharp sub-100 nm diameter dielectric tip and a wider base, a conductive layer coated on the core and extending to completely cover the dielectric tip to form a sharp exposed conductive tip of the nanowire, and a second dielectric covering electrode lead portions of the conductive layer below the sharp exposed conductive tip.

2. The nanowire electrode array of claim 1, further comprising a window in the substrate for simultaneous optical imaging and electrophysiological recording.

3. The nanowire electrode array of claim 1, wherein the sharp exposed conductive tips of the nanowires have a diameter of less than 20 nm.

4. The nanowire electrode array of claim 3, wherein the sharp exposed conductive tips of the nanowires have a diameter of less than 10 nm.

5. The nanowire electrode array of claim 4, wherein the sharp exposed conductive tips of the nanowires have a diameter of a few nm.

6. The nanowire electrode array of claim 3, wherein the nanowires have a diameter of about 60 nm at the base.

7. The nanowire electrode array of claim 3, wherein the nanowires have a height of 2 μm~15 μm.

8. The nanowire electrode array of claim 1, wherein the nanowires extend from a planar surface of the substrate.

9. The nanowire electrode array of claim 1, wherein the nanowires extend from a shaped surface of the substrate.

10. The nanowire electrode array of claim 8, wherein the shaped surface is a V-groove.

11. The nanowire electrode array of claim 1, wherein the electrode lead portions extend along a surface of the first dielectric on the substrate to provide a pattern that permits individual addressing of each nanowire electrode.

12. The nanowire electrode array of claim 10, wherein the pattern is covered with the second dielectric.

13. The nanowire electrode array of claim 11, further comprising contact pads in the pattern to connect to a recording system and that are exposed from the second dielectric.

14. The nanowire electrode array of claim 1, wherein the first dielectric is silicon dioxide unitary with and converted from silicon material of the substrate.

15. The nanowire electrode array of claim 1, wherein the first dielectric is germanium dioxide unitary with and converted from germanium material of the substrate.

16. A method for forming a nanowire electrode array comprising a plurality of vertical nanowires extending from a substrate, the method comprising:
   etching a substrate in a pattern that forms vertical cores of material extending away from remaining unetched portions of the substrate;
   thinning and converting the vertical cores and a surface of the substrate into first dielectric such that each core includes a sharp sub-100 nm diameter dielectric tip and a wider base;
   coating the vertical cores with a conductive layer that extends to a sharp exposed conductive tip over the dielectric tip; and
   protecting electrode lead portions of the conductive layer on a base portion below the exposed conductive tip with a second dielectric while leaving the exposed conductive tip uncovered.

17. The method of claim 15, wherein the etching comprises dry etching.

18. The method of claim 15, wherein said thinning and converting comprises multiple wet etching oxidation steps.

* * * * *